United States Patent [19]
Buchanan et al.

[11] Patent Number: 5,657,404
[45] Date of Patent: Aug. 12, 1997

[54] ROBUST SPECTROSCOPIC OPTICAL PROBE

[75] Inventors: Norma Lindsey Buchanan; Daniel Charles Alsmeyer; Gregory Wayne Nelson, all of Kingsport, Tenn.; Roger Dale Edwards, Blackwater, Va.; Vincent Alvin Nicely, Kingsport, Tenn.

[73] Assignee: Eastman Chemical Company, Kingsport, Tenn.

[21] Appl. No.: 450,597

[22] Filed: May 25, 1995

[51] Int. Cl.⁶ .................. G01J 3/44; G02B 23/26
[52] U.S. Cl. .................. 385/12; 356/301; 356/436; 385/139
[58] Field of Search .................. 356/246, 300, 356/301, 317, 318, 432, 436, 440; 385/12, 15, 31, 39, 138, 139, 902

[56] References Cited

U.S. PATENT DOCUMENTS

| | | | |
|---|---|---|---|
| 3,906,241 | 9/1975 | Thompson | 250/574 |
| 4,033,668 | 7/1977 | Presby | 385/95 |
| 4,488,773 | 12/1984 | Wagner | 385/12 |
| 4,573,761 | 3/1986 | McLachlan et al. | 385/115 |
| 4,707,134 | 11/1987 | McLachlan et al. | 356/342 |
| 4,802,761 | 2/1989 | Bowen et al. | 356/301 |
| 4,988,155 | 1/1991 | Harner et al. | 385/12 |
| 5,046,854 | 9/1991 | Weller et al. | 356/440 |
| 5,112,127 | 5/1992 | Carrabba et al. | 356/301 |
| 5,402,241 | 3/1995 | Jeannotte et al. | 356/436 |
| 5,402,508 | 3/1995 | O'Rourke et al. | 385/31 |
| 5,534,997 | 7/1996 | Schrader | 356/301 |

FOREIGN PATENT DOCUMENTS

94/20013  9/1994  WIPO.

OTHER PUBLICATIONS

Schwab et al., *Anal. Chem.*, 1984, vol. 56, pp. 2199–2204, "Versatile, Efficient Raman Sampling with Fiber Optics". [No Month].

*Primary Examiner*—John D. Lee
*Attorney, Agent, or Firm*—Cheryl J. Tubach; John F. Stevens; Harry J. Gwinnell

[57] ABSTRACT

Disclosed is a spectroscopic probe apparatus useful for Raman, near infrared, luminescence, ultraviolet or visible spectroscopies that is formed with a robust method of construction using a molten metal soldering technique. The disclosed method and apparatus provides an optical probe that is easy to manufacture yet able to withstand drastic environmental conditions without damage and produce useful spectroscopic results under such conditions.

26 Claims, 2 Drawing Sheets

ROBUST SPECTROSCOPIC OPTICAL PROBE

FIELD OF THE INVENTION

This invention relates to spectroscopic optical probes and more particularly to an optical probe of robust construction especially suitable for in situ spectroscopic measurements.

BACKGROUND OF THE INVENTION

Various spectroscopic techniques are routinely used to determine the constitution of chemical compositions and to monitor the progress of chemical reactions and processes. The choice of technique, including the wavelength of the radiation employed, depends on the information desired.

Infrared (IR) spectroscopy is based on the interaction with chemical substances of infrared irradiation having a wavelength between 0.77 μm and 1000 μm. A segment of IR spectroscopy, referred to as near infrared (NIR) spectroscopies, uses radiation wavelengths between 0.77 μm and 2.5 μm. IR and NIR spectroscopies generally involves the absorption of radiation as it passes through a sample. The absorption frequencies provide information regarding the chemical and physical characteristics or the molecular structure of the irradiated substance.

Ultraviolet (UV) and visible (VIS) spectroscopic methods employ UV radiation having wavelengths between 10 nm and 350 nm and visible radiation with wavelengths between 350 nm and 770 nm. UV/VIS techniques measure the absorption of the exposing radiation by molecular electronic transitions; the particular wavelengths absorbed are characteristic of the molecular structure of the substance under investigation.

Raman spectroscopy is another means by which chemical, physical, and molecular information of materials can be obtained. Incident radiation interacting with a material undergoes scattering, which occurs in all directions; the radiation may be scattered elastically or inelastically. The inelastically scattered radiation is referred to as Raman scatter. The wavelengths and intensities of this radiation comprise a Raman spectrum that provides chemical and structural information regarding the irradiated material.

Luminescence spectroscopy involves the measurement of photon emission from molecules. It includes photoluminescence such as fluorescence and phosphorescence, which are emissions from a substance resulting from its excitation by radiation absorption, and chemiluminescence, where the emission is induced by a chemical reaction. The emitted radiation is characteristic of the molecular structure.

All of these spectroscopic techniques are useful for gaining qualitative and quantitative information about a chemical material. IR, NIR, and Raman spectra, however, provide the greatest amount of molecular structural information.

Determining the constitution of a chemical composition or monitoring the progress of a chemical reaction is frequently carried out with materials situated in inhospitable environments. For example, analysis may be required of a process stream under conditions of high temperature and/or pressure or in the presence of corrosive substances or powerful solvents. It is well known to place spectrophotometric apparatus such as a spectrograph and a radiation source in a location remote from a substance that is to be analyzed in situ and connect the apparatus to the sampling site by radiation conduits comprising optical fibers. The interface between these optical fibers and the process environment is commonly provided by a probe, often referred to as a spectroscopic optical probe or a fiber optic probe.

A variety of spectroscopic probes are known in the art. U.S. Pat. No. 3,906,241, for example, describes a probe for use in analyzing fluids that incorporates three fiber optic channels, one to carry radiation from a source to the probe detecting head, a second to return radiation from the head, and a third to carry the scattered Raman radiation to detector means. In U.S. Pat. No. 4,573,761 is described a probe that comprises at least one optical fiber for transmitting light into a sample and at least two optical fibers for collecting radiation from the sample, the collecting fibers converging with the axis of the transmitting fiber at an angle less than 45 degrees. U.S. Pat. No. 4,707,134 describes a probe comprising a plurality of converging optical fibers contained in a housing that is closed at one end by a transparent window. A method for in situ detection of a compound by Raman spectroscopy is disclosed in U.S. Pat. No. 4,802,761, wherein a collecting cell is connected by an optical fiber bundle to a remote sensing device.

PROBLEM TO BE SOLVED BY THE INVENTION

As just noted, spectroscopic probes have been described in the prior art, and several such devices are available from various vendors. These known probes are frequently of complex design and thus expensive to manufacture; they may include, for instance, precisely aligned arrangements of multiple optical fibers, lenses, and windows, as well as gasketing materials and adhesives for assembling and sealing the probe component parts. In harsh process environments, such probes are susceptible to damage by high temperature and pressure and powerful chemical solvents, resulting in leakage, misalignment, and other forms of deterioration that adversely affect probe performance. Thus, there is a need for readily manufacturable spectroscopic probes whose robust design and construction allow their use in drastic environments without performance-degrading damage. This need is well met in the spectroscopic optical probe of the present invention.

SUMMARY OF THE INVENTION

In accordance with the invention, a fluid-tight spectroscopic optical probe comprises a fluid-tight housing, with a tip having a terminal surface sealably closing one end of the housing; at least one fiber optic excitation channel terminating at the terminal surface of the tip and extending within the length of the housing and transmitting radiation from a radiation source to a chemical composition that is to be irradiated for spectroscopic analysis; and at least one fiber optic collection channel terminating at the terminal surface of the tip and extending within the length of the housing and transmitting radiation from the irradiated composition to detector means remotely situated from the composition; wherein the fiber optic excitation and collection channels are securely held and sealed within the tip by solder means encompassing each channel.

A method for forming the spectroscopic optical probe of the invention comprises forming a cavity at the terminal surface of the tip and filling the cavity with molten metal solder, which is allowed to cool and solidify to a plug; forming closely spaced holes of circular cross-section that penetrate through the tip and the plug, the cross-section of the holes being very slightly larger than the cross-section of the optical fibers comprising the excitation and collection channels; inserting one end of each of the optical fibers into the holes through the tip and into the plug, the ends of the optical fibers forming a substantially continuous surface with the terminal surface of the tip; heating the solder plug to a temperature sufficient to cause the solder to flow around the optical fibers; cooling the plug to ambient temperature, thereby securing and sealing the optical fiber ends in the plug at the terminal surface of the tip; and grinding and polishing the substantially continuous terminal surface of the tip to form an optically smooth terminal surface.

ADVANTAGEOUS EFFECT OF THE INVENTION

The present invention provides an optical probe that is easy to manufacture yet able to withstand drastic environmental conditions without damage and produce useful spectroscopic results under such conditions.

DETAILED DESCRIPTION OF THE INVENTION

Figure 1:
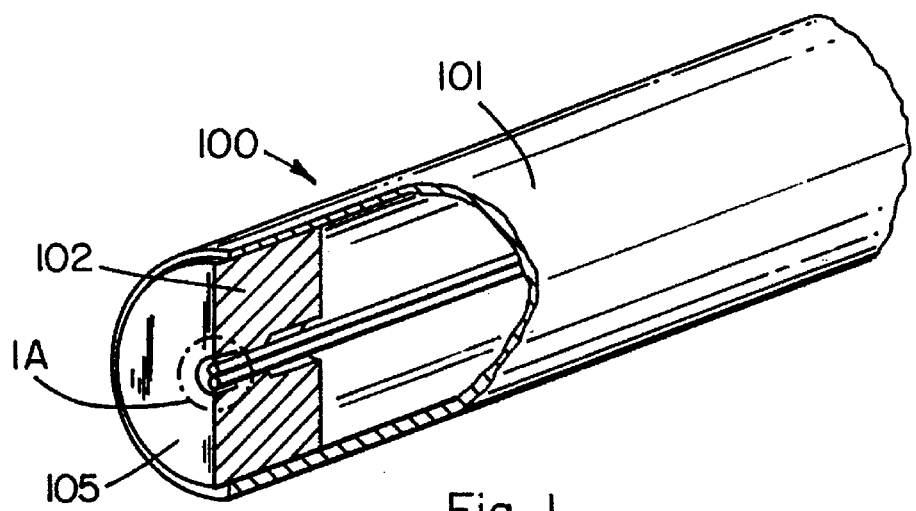
FIG. 1 is a fragmentary isometric view, partially in section, of a preferred embodiment.
Figure 1A:
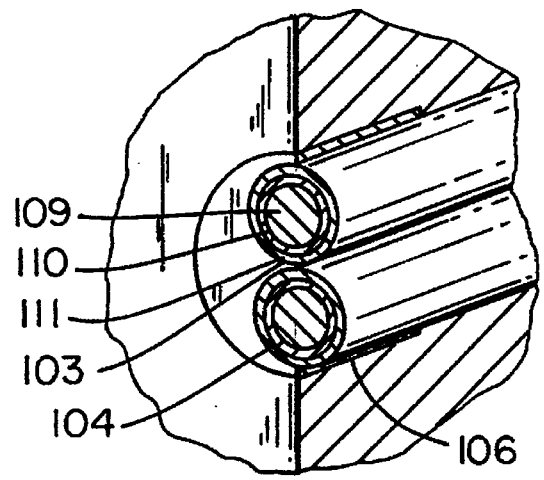
FIG. 1A is a fragmentary isometric view, partially in section, depicting in detail the optical fiber ends at the probe tip of the preferred embodiment in FIG. 1.
Figure 3:
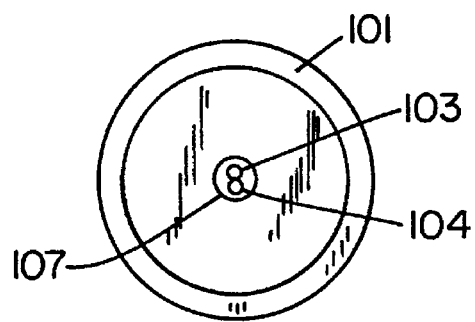
FIG. 3 is an end elevational view of the embodiment of FIG. 1.
Figure 2:
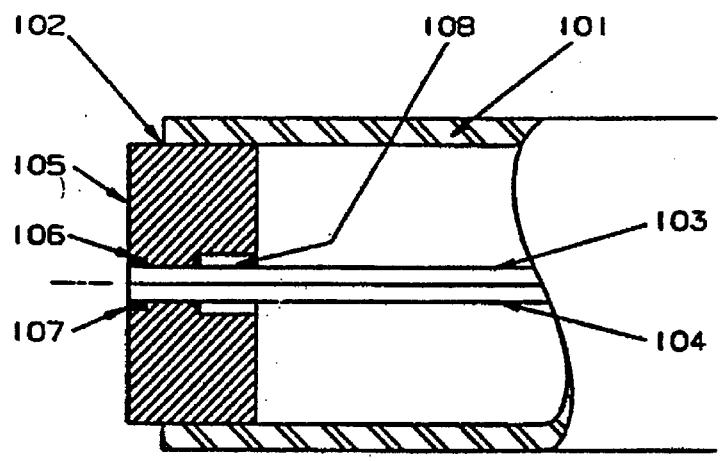
FIG. 2 is a fragmentary cross-section of the embodiment of FIG. 1.

In FIGS. 1, 2, 3 is shown a preferred embodiment of the present invention. Optical probe 100 comprises a housing 101, closed at one end by tip 102. Two optical fibers 103 and 104, one serving as an excitation channel for radiation from a source to a composition to be analyzed, the other comprising a collection channel for transmitting radiation from the irradiated composition to remotely situated detector means, extend from the terminal surface 105 of the tip through the length of the housing. The depicted embodiment includes a single excitation channel and a single collection channel, which simplifies its construction. As taught in U.S. Pat. No. 4,707,134, the disclosures of which are incorporated herein by reference, a single fiber is sufficient to transmit light from a light emitting diode, a laser, or a diode laser. However, a probe of the invention may contain two to six fiber optic collection and/or excitation channels. In one useful configuration of the fibers, a single excitation channel within a bundle is surrounded by six collection channels, as shown in U.S. Pat. No. 4,573,761, the disclosures of which are incorporated herein by reference.

On the terminal surface 105 of tip 102 is formed a cavity 106, which is filled with molten metal solder that solidifies on cooling to a solder plug 107. This plug comprises means for securing and sealing the ends of the optical fibers at the terminal surface of the probe tip.

In the construction of the probe of the invention, closely spaced holes of circular cross-section very slightly larger than the fiber cross-section are drilled through the tip and the solder plug. An optical fiber is inserted in each hole to fill it, the end of each fiber forming a substantially continuous surface with the terminal surface of the tip. A cavity 108 may be formed in the back of the tip to facilitate insertion of the fibers into the holes.

The solder plug is heated to a temperature sufficient to cause the solder to flow around the optical fiber ends. During heating; a small additional quantity of solder may be applied to the plug to compensate for settling. On cooling of the plug to ambient temperature, the fibers are sealed and secured at the terminal surface of the tip. Subsequent grinding and polishing of the tip terminal surface provides an optically smooth surface.

In sealing and securing the optical ends at the terminal surface of the tip, the heating of the solder plug must be carefully controlled to avoid softening the quartz glass of the fiber. Damage to the fibers would be highly likely should one attempt to secure them by drilling holes large enough to accommodate them through the tip (which is preferably made of stainless steel), inserting the fiber ends in the holes, and then applying solder to effect sealing. In accordance with the method of the invention, the likelihood of damage to the fibers is minimized by the formation of the solder plug at the tip terminal surface prior to the drilling of the holes to receive the fibers. The holes should be of a diameter just large enough to allow the fibers to be inserted into them; the solder plug is then heated to a point just sufficient to cause the solder to flow around the fiber ends, so that on cooling the ends are secured and sealed in the tip. To further reduce the amount of heat required for sealing and also to avoid uneven expansion within the probe tip during use, it is desirable that the size of the solder plug be of the minimum size necessary to ensure secure sealing of the fibers.

The optical fibers utilized in the probe of the invention are preferably step-indexed multimode fibers, which are available from several commercial sources, for example, Fiberguide, Stirling, N.J. Their diameters may range from 1 µm to 1000 µm, preferably 200 µm to 400 µm. For Raman and luminescence spectroscopy fibers of about 200 µm diameter are preferred; for UV/VIS and NIR measurements, fibers with diameters of about 400 µm are preferred.

Preferred optical fibers for the present invention comprise a quartz glass core 109 surrounded by a thin inner layer of doped quartz 110, and then by a thin solder-adherable metallic outer layer 111, preferably of gold. The metallic layer 111 facilitates adhesion of the fiber to the solder plug, as described in U.S. Pat. No. 4,033,668, the disclosures of which are incorporated herein by reference.

The housing and tip of the probe can be constructed from various metallic materials, for example, copper or titanium. Preferred metals for this purpose include Hastalloy and stainless steel. The solder employed to seal and secure the optical fiber ends in the tip should be resistant to chemical deterioration and have a fusion temperature high enough to withstand the drastic conditions to which the probe may be subjected during use. A presently preferred embodiment can be employed without damage at temperatures of about 500° C. and pressures ranging up to 30,000 psi. Of course, the solder fusion temperature should also be sufficiently low to achieve sealing of the optical fibers without softening of the glass. Preferred soldering material for securing the optical fiber ends, with fusion temperatures in the range of about 600° C. to 1100° C., are silver or gold solders; other types of solders may be employed to connect the probe tip to the housing.

In constructing the probe, a small amount of additional length, up to about 0.5 percent of the total, is provided in the optical fibers extending through the housing away from the tip. This slack is desirable to prevent stresses and cracking of the fibers as the metal components of the probe expand at different rates than the optical glass at high temperatures. The ends of the fibers remote from the tip are connected with the radiation source and spectrograph by connecting means well known in the art, for example, SMA connectors.

The detector means, which may be an ultraviolet-visible (UV/VIS), a near infrared (NIR), a luminescence, or a Raman spectrometer, and the radiation source may be situated at a distance from and connected to the probe by optical fibers, as described in U.S. Pat. No. 4,802,761, the disclosures of which are incorporated herein by reference. The type of radiation source depends on the particular spectrometry; useful sources include, for example, argon, hydrogen, deuterium, xenon, and tungsten lamps for UV/VIS; nichrome wires, Nernst glowers, and halogen-modified tungsten lamps for NIR/IR; and lasers, especially diode lasers, for Raman and luminescence spectrometry.

Following construction, the probe may be inserted into a line or a reactor within a process and secured therein in a fluid-tight fashion by means such as, for example, a threaded, soldered, or otherwise sealable connection. Although the robust construction of the probe of the invention makes it especially useful for monitoring chemical compositions in harsh environments characterized by high temperatures and pressures, it is not restricted to such applications. A probe may be constructed, in accordance with the method of the invention, with shape and dimensions suitable for in situ analyses, Raman spectrometric measurements for example, in living organisms, as described in U.S. Pat. No. 3,906,241, the disclosures of which are incorporated herein by reference.

Figure 4:
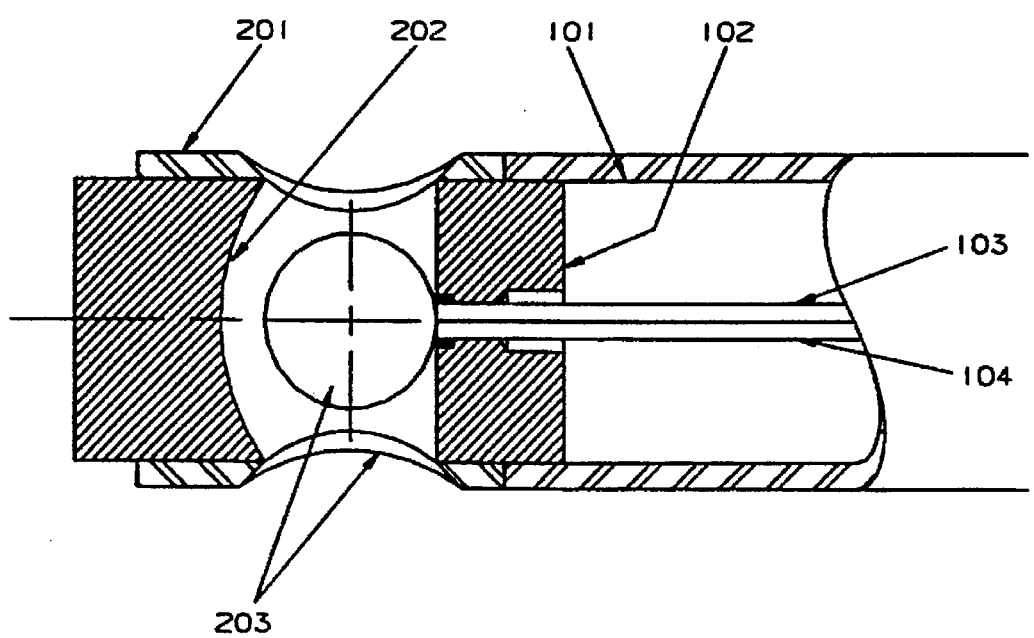
FIG. 4 is a fragmentary cross-section of an embodiment that includes a reflector cap with a concave mirror.

Fiber optic probes such as those of the present invention are particularly useful for Raman spectrometric measurements, as described in Schwab et al., Anal. Chem., 1984, vol. 56, pages 2199–2204, the disclosures of which are incorporated herein by reference. A probe of the invention may also be utilized for transmittive/reflective spectroscopy such as UV/VIS and NIR measurements. FIG. 4 depicts the embodiment of FIG. 1 further comprising a reflector cap 201 that includes a concave mirror 202 and is provided with flow-through ports 203. The ports enable the chemical composition to flow over the probe tip, and the mirror is constructed with appropriate curvature and is positioned at the proper distance at the tip to maximize the amount of radiation from the irradiated composition that is gathered by the collection channel.

The present invention provides an optical probe of simple design and ready manufacturability whose robust construction enables its prolonged use for obtaining reliable spectrometric measurements, even in harsh environments of elevated temperature and pressure. The excellent performance of the probe of this invention under such conditions contrasts with that of several probes that are commercially available from various vendors and are advertised as able to withstand elevated pressures as well as temperatures as high as 300° C. In a polymer production process at temperatures of 200°–300° C., under which conditions a probe of the invention yielded reliable measurements over a prolonged period, one commercially available probe that included optical rods, lenses, and windows cemented into a metal housing quickly failed as a result of the rods becoming loose and misaligned. In another commercial probe of a different design, the epoxy resin employed to hold the fibers of a bundle in place carbonized and decomposed during a brief trial under the process conditions. In still another instance, the protective window seal of the probe failed, resulting in leakage of the polymer into the chamber containing the optical fibers. Finally, during testing of another commercial probe touted as able to withstand 300° C. and high pressure, its protective sapphire window was lost to the production stream and never recovered. These repeated failures of a variety of commercially available optical probes after limited exposure to harsh process environments attest to the remarkable and unexpected advantages provided by the robust probe of the present invention.

The following examples further illustrate the invention.

EXAMPLE 1—Raman Probe for Monitoring a Batch Chemical Reaction

A fiber optic probe was constructed as shown in FIGS. 1–3. Two 400-µm inner diameter gold coated fiber optics purchased from Fiberguide, Stirling N.J., were silver soldered using Safety Silv® 45 solder obtained from J. W. Harris Co., Cincinnati, Ohio, into a 0.25 inch diameter 316 stainless steel tube body. Upon cooling, the probe tip was polished to a mirror finish. A test of the probe for signal throughput confirmed its efficiency. The probe was used to monitor a chemical reaction by Raman spectrometry over a period of three hours, during which the temperature reached 220° C. Excellent spectral data were collected, and the probe showed no signs of degradation.

EXAMPLE 2—Raman Probe for Monitoring a Manufacturing Process

A fiber optic probe was constructed similar as shown in FIGS. 1–3. Two 200-µm inner diameter gold coated fiber optics purchased from Fiberguide, Stirling N.J., were silver soldered into a 0.25 inch diameter 316 stainless steel tube. Upon cooling, the probe tip was polished to a mirror finish and subsequently tested for signal throughput. The probe was placed in a process stream of a manufacturing installation and connected to a Raman analytical instrument. The process was operated at pressures between 15 to 30 psi and temperatures between 200° C. and 230° C. After several months of successful spectral acquisition, the probe was removed from the process. Inspection of the probe following removal showed that it had robustly survived the lengthy exposure to the process environment.

EXAMPLE 3—NIR Probe for Monitoring a Manufacturing Process

A fiber optic probe for NIR spectroscopy was designed and constructed with a reflector cap containing a concave mirror, as shown in FIG. 4. Two 400-µm inner diameter gold coated fiber optics were silver soldered into a 0.25 inch diameter 316 stainless steel tube. Upon cooling, the probe tip was polished to a smooth, mirror-like finish. A reflector comprising a concave mirror was fastened above the probe tip to complete the probe assembly. This probe was placed in a manufacturing process stream operating at temperatures up to 300° C. and pressures up to 1000 psi. After two months of spectroscopic measurements, the probe was removed from the process. Inspection of the probe after its removal confirmed that it had withstood the prolonged exposure to the harsh conditions of the process.

EXAMPLE 4—Probe for UV/VIS Monitoring of Color in an Extruder

The fiber optic probe of Example 3 was inserted into an extruder and used to monitor the UV/VIS spectrum of a molten polymer. The operating conditions of the stream were temperatures up to 315° C. and pressures up to 250 psi. The probe performed well over several days of testing.

The invention has been described in detail with particular reference to preferred embodiments thereof, but it will be understood that variations and modifications can be effected within the spirit and scope of the invention.

We claim:

1. A fluid-tight spectroscopic optical probe comprising:
   (a) a fluid-tight housing;
   (b) a probe tip having a terminal surface, said probe tip sealably closing one end of said housing;
   (c) at least one fiber optic excitation channel terminating at said terminal surface of said probe tip and extending within the length of said housing, said excitation channel transmitting radiation from a radiation source to a chemical composition to be irradiated for spectroscopic analysis; and
   (d) at least one fiber optic collection channel terminating at said terminal surface of said probe tip and extending within the length of said housing, said collection channel transmitting radiation from an irradiated chemical composition to detector means remotely situated from said chemical composition;
   wherein said fiber optic excitation channel and said fiber optic collection channel are each separated from one another and securely held and sealed within said probe tip by solder means encompassing each said channel.

2. The probe of claim 1 comprising two to six fiber optic collection channels.

3. The probe of claim 1 comprising two to six fiber optical excitation channels.

4. The probe of claim 1 wherein said housing and tip are formed from solder-adherable metal.

5. The probe of claim 4 wherein said metal is stainless steel.

6. The probe of claim 1 wherein said excitation channel and said collection channel each comprises an optical fiber having a circular cross-section, said fibers having a diameter of 1 μm to 1000 μm.

7. The probe of claim 6 wherein said diameter is 200 μm to 400 μm.

8. The probe of claim 6 wherein each said optical fiber further comprises a peripheral surface bearing a thin solder-adherable metallic layer.

9. The probe of claim 8 wherein said metallic layer comprises gold.

10. The probe of claim 6 wherein each said optical fiber comprises a step-indexed multimode optical fiber.

11. The probe of claim 1 wherein said solder means comprises a solder plug, said plug being situated at said terminal surface of said tip.

12. The probe of claim 11 wherein said solder plug is formed of a silver solder or a gold solder.

13. The probe of claim 1 further comprising a reflector cap that includes a concave mirror, said cap being situated in close proximity to said tip and capable of reflecting radiation from said excitation channel to said collection channel.

14. The probe of claim 1 wherein said detector means comprises a spectrometer.

15. The probe of claim 14 wherein said spectrometer is an ultraviolet-visible (UV/VIS) spectrometer, a near infrared (NIR) spectrometer, a Raman spectrometer, or a luminescence spectrometer.

16. The probe of claim 15 wherein said spectrometer is a Raman spectrometer and said radiation source is a laser.

17. The probe of claim 16 wherein said laser is a diode laser.

18. The probe of claim 15 wherein said spectrometer is a near infrared (NIR) spectrometer and said radiation source is a halogen-modified tungsten lamp.

19. The probe of claim 15 wherein said spectrometer is an ultraviolet-visible (UV-VIS) spectrometer and said radiation source is a tungsten lamp.

20. The probe of claim 1 comprising a single fiber optic excitation channel.

21. The probe of claim 1 comprising a single fiber optic collection channel.

22. A method for forming a fluid-tight spectroscopic optical probe provided with a fluid-tight housing and a probe tip having a terminal surface and sealably closing one end of said housing, said housing and said probe tip each being formed of solder-adherable metal; at least one excitation channel that transmits radiation from a radiation source to a chemical composition to be irradiated; and at least one collection channel that transmits radiation from an irradiated chemical composition to detector means remotely situated from said chemical composition, each said channel comprising an optical fiber having a circular cross-section, one end of each said fiber terminating at said terminal surface of said probe tip and extending within the length of said housing; said method comprising:

forming a cavity at said terminal surface of said probe tip;

filling said cavity with molten metal solder, then allowing said solder to cool and solidify to a plug;

forming at least two closely spaced holes of circular cross-section penetrating through said plug, said holes having a cross-section very slightly larger than the cross-section of said optical fibers;

inserting one end of each of said optical fibers through said probe tip and into each of said holes in said plug, thereby substantially filling said holes in said probe tip and plug, said ends of said fibers being separated from one another and together with said plug forming a substantially continuous surface with said terminal surface of said probe tip;

heating said solder plug to a temperature sufficient to cause the solder to flow around and encompassing each said optical fiber end;

cooling said plug to ambient temperature, thereby securing and sealing said separated optical fiber ends at said terminal surface of said probe tip; and grinding and polishing said substantially continuous terminal surface of said probe tip, thereby forming an optically smooth terminal surface.

23. The method of claim 22 wherein said solder plug is formed of a silver solder or a gold solder.

24. The method of claim 22 further comprising:
   sealably connecting said housing with said probe tip by soldering.

25. The method of claim 22 wherein each said optical fiber further comprises a peripheral surface bearing a thin solder-adherable layer of gold.

26. The method of claim 22 wherein each said optical fiber has a diameter of about 200 μm to 400 μm.

* * * * *